United States Patent
Rasmussen et al.

[11] Patent Number: 6,110,884
[45] Date of Patent: Aug. 29, 2000

[54] PROTEASE VARIANTS

[75] Inventors: Grethe Rasmussen; Egon Nielsen, both of Copenhagen; Torben Halkier, Frederiksberg, all of Denmark

[73] Assignee: Novo Nordisk A/S, Bagsvaerd, Denmark

[21] Appl. No.: 09/460,658

[22] Filed: Dec. 13, 1999

Related U.S. Application Data

[60] Division of application No. 08/852,790, May 7, 1997, which is a continuation-in-part of application No. 08/522,283, Sep. 13, 1995, abandoned, which is a continuation-in-part of application No. PCT/DK94/00133, Mar. 29, 1993.

[51] Int. Cl.[7] ............................ C11D 3/396; C12N 9/54; C12N 15/00
[52] U.S. Cl. ..................... 510/392; 510/321; 510/320; 510/530; 485/219; 485/220; 485/221; 485/222; 485/223; 485/224
[58] Field of Search ................................ 435/219, 220, 435/221, 222, 223, 224; 510/392, 320, 530, 321, 226

[56] References Cited

FOREIGN PATENT DOCUMENTS

| | | |
|---|---|---|
| 0251446 | 1/1988 | European Pat. Off. . |
| 0 251 446 | 7/1988 | European Pat. Off. . |
| 0945502 | 7/1992 | European Pat. Off. . |
| 0769549 | 4/1997 | European Pat. Off. . |
| 92/11348 | 7/1992 | WIPO . |
| 92/11357 | 7/1992 | WIPO . |
| WO 92/11348 | 7/1992 | WIPO . |
| WO 92/11357 | 7/1992 | WIPO . |

*Primary Examiner*—Kery Fries
*Attorney, Agent, or Firm*—Steve T. Zelson; Valeta Gregg

[57] ABSTRACT

This invention is a protease mutant wherein said mutant substitutes the naturally occurring tyrosine amino acids for other amino acids at positions 91, 167, 171, 192, 209, 214, and 263. The protease mutants are used in detergent compositions.

8 Claims, 1 Drawing Sheet

PROTEASE VARIANTS

CROSS-REFERENCES TO RELATED APPLICATIONS

This application is a divisional of application Ser. No. 08/852,790 filed May 7, 1997 which is a continuation of application Ser. No. 08/522,283 filed Sep. 13, 1995, abandoned, which is a continuation of PCT/DK94/00133 filed Mar. 29, 1993 and claims priority under 35 U.S.C. 119 of Danish application 0390/93 filed Apr. 1, 1993, the contents of which are fully incorporated herein by reference.

FIELD OF INVENTION

The present invention relates to protease variants, stabilized towards the inactivation caused by peroxidase systems, in which protease variants a naturally occurring tyrosine residue has been deleted or substituted with a different amino acid residue at one or more positions.

The invention also relates to a method of stabilizing a protease towards the inactivation caused by peroxidase systems, and detergent compositions comprising a protease variant of the invention.

BACKGROUND ART

Peroxidases (E.C. 1.11.1.7) are enzymes that catalyse the oxidation of a substrate (an electron or hydrogen donor) with hydrogen peroxide. Such enzymes are known from microbial, plant and animal origins, e.g. peroxidase from *Coprinus cinereus* (cf. e.g. EP Patent Application 179,486). They are typically hemoproteins, i.e. they contain a heme as a prosthetic group.

Use of peroxidase together with hydrogen peroxide or a hydrogen peroxide precursor has been suggested e.g. in bleaching of pulp for paper production, in treatment of waste water from pulp production, for improved bleaching in laundry detergents, for dye transfer inhibition during laundering, and for lignin modification, e.g. in particle board production.

Peroxidase systems (also designated POD systems) comprising an enzyme exhibiting peroxidase activity, a source of hydrogen peroxide, and a peroxidase enhancing agent, are used for preventing surplus dyes from coloured fabrics which leach from the fabrics when these are washed from being deposited on other fabrics present in the same wash (this phenomenon is commonly known as dye transfer). Detergent compositions or wash liquors comprising such peroxidase systems have been described in WO 92/18687 and WO 92/18683.

A major drawback in applying such peroxidase systems to detergent compositions is that the enzymes present in such compositions may be strongly affected by the peroxidase system, thereby hampering the washing performance of the detergent composition.

SUMMARY OF THE INVENTION

It has now surprisingly been found that proteolytic enzymes are stabilized towards inactivation caused by peroxidase systems, by deletion or substitution of one or more naturally occurring tyrosine residues with a different amino acid residue.

Accordingly, the invention provides a protease variant, in which one or more naturally occurring tyrosine residues have been deleted or substituted with a different amino acid residue.

In another aspect, the invention provides a method of stabilization of a protease towards inactivation caused by a peroxidase system, in which method one or more naturally occurring tyrosine residues are deleted or substituted with a different amino acid residue.

In a further aspect, the invention provides detergent compositions comprising a protease variant of the invention.

In a yet further aspect, the invention provides detergent additives comprising a protease variant of the invention.

BRIEF DESCRIPTION OF DRAWINGS

The present invention is further illustrated by reference to the accompanying drawings, in which.

DETAILED DISCLOSURE OF THE INVENTION

Figure 1:
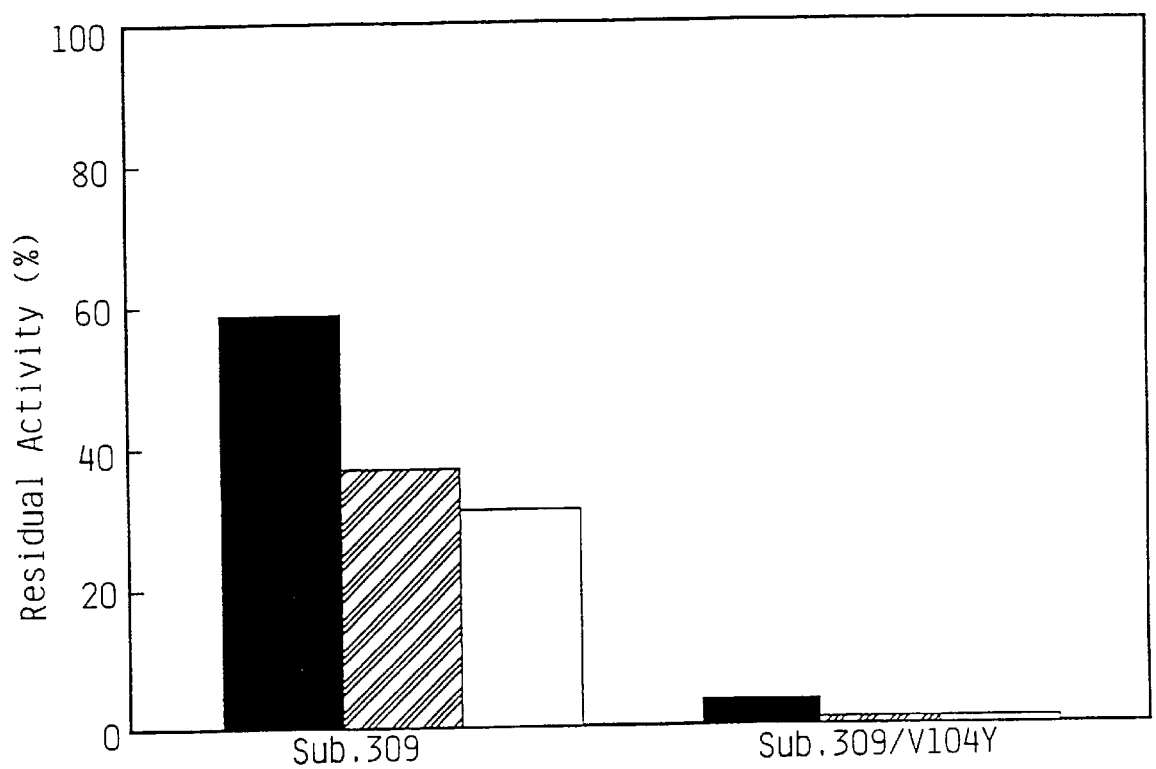
FIG. 1 shows the residual activity(%)—after 1 min. (black), 5 min. (hatched) and 10 min. (white)—of Subtilisin 309 and Subtilisin 309/V104Y at 35° C. in the presence of POD system as described in Example 4.

The present invention provides novel protease variants, stabilized towards inactivation caused by peroxidase systems.

In the context of this invention, a stabilized protease is a protease variant or a mutated protease having improved stability towards inactivation caused by peroxidase systems, when compared to the parent enzyme. By a protease variant or a mutated protease is meant a protease obtainable by alteration of a DNA nucleotide sequence of the parent gene or its derivatives. The protease variant or the mutated protease may be expressed and produced when the DNA nucleotide sequence encoding the enzyme is inserted into a suitable vector in a suitable host organism. The host organism is not necessarily identical to the organism from which the parent gene originated.

Amino Acids

As abbreviations for amino acids the following symbols are used:

| | | |
|---|---|---|
| A= | Ala= | Alanine |
| C= | Cys= | Cysteine |
| D= | Asp= | Aspartic acid |
| E= | Glu= | Glutamic acid |
| F= | Phe= | Phenylalanine |
| G= | Gly= | Glycine |
| H= | His= | Histidine |
| I= | Ile= | Isoleucine |
| K= | Lys= | Lysine |
| L= | Leu= | Leucine |
| M= | Met= | Methionine |
| N= | Asn= | Asparagine |
| P= | Pro= | Proline |
| Q= | Gln= | Glutamine |
| R= | Arg= | Arginine |
| S= | Ser= | Serine |
| T= | Thr= | Threonine |
| V= | Val= | Valine |
| w= | Trp= | Tryptophan |
| Y= | Tyr= | Tyrosine |
| B= | Asx= | Asp (D) or Asn (N) |
| Z= | Glx= | Glu (E) or Gln (Q) |
| X= | an arbitrary amino acid | |
| *= | deletion or absent amino acid | |

Peroxidase Activity

In the context of this invention, the enzymatic activity of peroxidases is expressed in "Peroxidase Units" (PODU). In the presence of hydrogen peroxide peroxidases (E.C. 1.11.1.7) catalyse the dehydrogenation of 2,2'-azino-bis(3- ethylbenzothiazoline-6-sulfonate) (ABTS). The greenish-blue colour produced is monitored photometrically at 418 nm. One PODU is the amount of enzyme which, under standard conditions (i.e. pH 7.0; hydrogen peroxide as substrate; 0.1 M phosphate buffer; an incubation temp. of 30° C.; an incubation time of 3 min. measured kinetically) catalyses the conversion of 1 μmol of hydrogen peroxide per minute.

Protease Activity

In the context of this invention, the enzymatic activity of subtilisins was measured using chromogenic substrates. Incubation of proteases with these substrates results in the cleavage of the substrate and liberation of p-nitroaniline that is detected spectrophotometrically at 405 nm.

Subtilisins are analyzed using the substrate N-succinyl-Ala-Ala-Pro-Phe-p-nitroanilide (0.8 mM in 20 mM sodium phosphate buffer, pH 8.5 or 0.8 mM in 20 mM Britton-Robinson buffer, pH 8.5). The incubation is carried out at 25° C. and followed spectrophotometrically for 4 min. The concentration of the protease is chosen so that the liberation of p-nitroaniline is linear during the whole analysis.

Peroxidase Systems

In the context of this invention, a peroxidase system is a system comprising a peroxidase or a compound exhibiting peroxidase activity, a source of hydrogen peroxide, and a peroxidase enhancing agent. Such peroxidase systems have been used for obtaining a dye transfer inhibition and have been described in e.g. International Patent Applications WO 92/18687 and WO 92/18683.

In such a peroxidase system, the peroxidase or the compound exhibiting peroxidase activity may be any peroxidase comprised by the enzyme classification EC 1.11.1.7, or any fragment derived therefrom, exhibiting peroxidase activity, or synthetic or semisynthetic derivatives thereof (e.g. porphyrin ring systems or microperoxidases, cf. e.g. U.S. Pat. No. 4,077,768, EP Patent Application 537,381, International Patent Applications WO 91/05858 and WO 92/16634). Such peroxidases are known from microbial, plant and animal origins.

The peroxidase may be producible by plants (e.g. horseradish or soy bean peroxidase) or microorganisms such as fungi or bacteria. Some preferred fungi include strains belonging to the subdivision Deuteromycotina, class Hyphomycetes, e.g. Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes.*

Other preferred fungi include strains belonging to the subdivision Basidiomycotina, class Basidiomycetes, e.g. Coprinus, Phanerochaete, Coriolus or Trametes, in particular *Coprinus cinereus* f. microsporus (IFO 8371), *Coprinus macrorhizus, Phanerochaete chrysosporium* (e.g. NA-12) or Trametes (previously called Polyporus), e.g. *T. versicolor* (e.g. PR4 28-A).

Further preferred fungi include strains belonging to the subdivision Zygomycotina, class Mycoraceae, e.g. Rhizopus or Mucor, in particular *Mucor hiemalis.*

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium.*

Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to Myxococcus, e.g. *M. virescens.*

Other potential sources of useful particular peroxidases are listed in Saunders B C et al., Peroxidase, London Butterworths, 1964, pp. 41–43.

The peroxidase may furthermore be one which is producible by a method comprising cultivating a host cell transformed with a recombinant DNA vector which carries a DNA sequence encoding said peroxidase as well as DNA sequences encoding functions permitting the expression of the DNA sequence encoding the peroxidase, in a culture medium under conditions permitting the expression of the peroxidase and recovering the peroxidase from the culture.

Particularly, a recombinantly produced peroxidase is a peroxidase derived from a Coprinus sp., in particular *C. macrorhizus* or *C. cinereus* according to WO 92/16634.

In the context of this invention, compounds exhibiting peroxidase activity comprise peroxidase active fragments derived from cytochromes, hemoglobin or peroxidase enzymes, and synthetic or semisynthetic derivatives thereof, e.g. iron porphins, iron porphyrins, and iron phthalocyanine and derivatives thereof.

In a peroxidase system, the enhancer may be an oxidizable substrate e.g. metal ions or phenolic compounds such as 7-hydroxycoumarin (7HCm), vanillin (VAN), and p-hydroxybenzenesulfonate (pHBS), described in e.g. International Patent Applications WO 92/18683 and WO 92/18687, and Kato M and Shimizu S, Plant Cell Physiol. 1985 26 (7), pp. 1291–1301 (cf. Table 1 in particular), and Saunders B C et al., Peroxidase, London Butterworths, 1964, p. 141 ff. or 2,2'-azino-bis (3-ethylbenzothiazoline-6-sulfonate) (ABTS), described in WO 93/00394.

Protease Variants

A protease variant of the invention, stabilized towards inactivation caused by peroxidase systems, may be a variant of any proteolytic enzyme suited for incorporation into detergents.

In the context of this invention, such proteolytic enzymes comprise alkaline proteases, subtilisins (e.g. *Bacillus lentus* proteases, *Bacillus amyloliquefaciens* proteases and *Bacillus licheniformis* proteases), trypsin-like proteases (e.g. Fusarium proteases, International Patent Application WO 89/06270), and lytic proteases (e.g. Nocardiopsis proteases, International Patent Application WO 88/03947).

Subtilisins

In the context of this invention, a subtilisin is defined as a serine protease produced by gram-positive bacteria or fungi. According to another definition, a subtilisin is a serine protease, wherein the relative order of the amino acid residues in the catalytic triad is Asp-His-Ser (positions 32, 64, and 221, BPN' numbering).

Preferred subtilisins are *Bacillus lentus* proteases, e.g. Subtilisin 309 and Subtilisin 147, *Bacillus amyloliquefaciens* proteases, e.g. Subtilisin BPN', and *Bacillus licheniformis* proteases, e.g. Subtilisin Carlsberg.

Amino Acid Numbering

In the context of this invention, a specific numbering of amino acid residue positions in subtilisins is employed. By alignment of the amino acid sequences of various subtilisins along with Subtilisin BPN' it is possible to allot a number to the amino acid residue position in any subtilisin to the number of the analogous amino acid position in Subtilisin BPN' ("BPN' numbering", vide e.g. International Patent Applications WO 89/06279 and WO 91/00345).

In describing the various protease variants produced or contemplated according to the invention the following nomenclatures were adapted for ease of reference:

Original amino acid; Position; Substituted amino acid

Accordingly, the substitution of tyrosine with phenylalanine in position 209 is designated as:

Y209F

Deletion of an aspartic acid at position 36 is indicated as: D36*, and an insertion in such a position is indicated as: 36D for insertion of an aspartic acid in position 36.

Multiple mutations are separated by plusses, i.e.:

Y167I+Y209F representing mutations in positions 167 and 209, substituting tyrosine with isoleucine and phenylalanine, respectively.

If a substitution is made by mutation in e.g. Subtilisin 309, the product is designated e.g. "Subtilisin 309/Y209F".

All positions in respect of subtilisins mentioned in this context refer to the BPN' numbers described above.

In a preferred embodiment, the protease variant of the invention is a subtilisin that has been changed in one or more of the following positions: 6, 57, 91, 104, 143, 167, 171, 192, 206, 209, 214, 256, 262, 263, more preferred 104, 167, 171, 192 (BPN' numbering).

In another preferred embodiment, the protease variant of the invention is Subtilisin 309, Subtilisin 147, Subtilisin BPN', or Subtilisin Carlsberg.

Methods of Stabilizing Proteases

The present invention provides a method of stabilizing proteolytic enzymes towards inactivation caused by peroxidase systems, by which method one or more naturally occurring tyrosine residues are deleted or substituted with a different amino acid residue.

Recombinantly Produced Enzymes

In the past, numerous processes have been developed for the production of polypeptides or proteins by means of the recombinant DNA technology. Mostly used for this purpose are E. coli, Bacillus subtilis, Saccharomyces cerevisiae and different Aspergillus strains, e.g. A. orvzae and A. niger.

Expression of Polypeptides Biosynthetically

Upon transformation of an organism where the intention is production of a polypeptide or a protein, a DNA sequence is introduced into the organism. The sequence contains the coding region of the gene of interest flanked by transcription/translation start signals and transcription/translation termination signals. The coding region contains units of three base pairs, called codons, which upon translation of the transcribed gene are translated into amino acids, which again are assembled to give the polypeptide of interest.

Introducing Mutations in Polypeptides

By changing one or more specific codons in the coding region and transforming the host microorganism with these new coding regions, new polypeptides can be produced which differ from the original polypeptide by one or more amino acids. Such alterations can be introduced by means of a technique generally known as "site-directed in vitro mutagenesis". A number of methods have been published. An early method is described by Zoller & Smith, DNA 1984 3 (6) 479–488, and involves use of the single-stranded M13 bacteriophage. A preferred method using PCR (polymerase chain reaction) is described by Nelson & Long,. Analytical Biochemistry, 1989 180 147–151. It involves a 3-step generation of a PCR fragment containing the desired mutation by using a chemically synthesized DNA oligonucleotide as one of the primers in the PCR reactions. From the PCR-generated fragment, a DNA fragment carrying the mutation can be isolated by cleavage with restriction enzymes and re-inserted into the expression plasmid. A third mutagenesis method takes advantage of restriction sites in the DNA coding region. By digesting the DNA with restriction enzymes at sites flanking the mutagenesis target, synthesizing a new fragment synthetically containing the desired mutation and cloning this new fragment between the restriction sites, a mutant coding region can be constructed.

All methods are generally applicable to investigations in the field called protein engineering which deals with the development of polypeptides with new or altered characteristics.

Transformation and expression may be accomplished by methods known in the art, e.g. as described in European Patent Application 305,216, which specification is hereby included by reference.

The microorganisms able to produce a stabilized enzyme of this invention can be cultivated by conventional fermentation methods in a nutrient medium containing assimilable carbon and nitrogen together with other essential nutrients, the medium being composed in accordance with the principles of the known art. Purification and recovery of the stabilized enzyme may also be conducted in accordance with methods known per se.

Cloning a Protease Gene

The gene encoding the proteolytic enzyme may be cloned from any Gram-positive bacteria or fungus by various methods well known in the art. First a genomic, and/or cDNA library of DNA must be constructed using chromosomal DNA or messenger RNA from the organism that produces the protease to be studied. Then, if the amino-acid sequence of the protease is known, homologous oligonucleotide probes may be synthesized, labelled, and used to identify protease-encoding clones from a genomic library of bacterial DNA, or from a fungal cDNA library. Alternatively, a labelled oligonucleotide probe containing sequences homologous to protease from another strain of bacteria or fungus could be used as a probe to identify protease-encoding clones, using hybridization and washing conditions of lower stringency.

Yet another method for identifying protease-producing clones would involve inserting fragments of genomic DNA into an expression vector such as a plasmid, transforming protease-negative bacteria with the resulting genomic DNA library, and then plating the transformed bacteria onto agar containing a substrate fbr protease, such as skim-milk. Those bacteria containing protease-bearing plasmid will produce colonies surrounded by a halo of clear agar, due to digestion of the skim-milk by excreted proteolytic enzyme.

Generation of Site Directed Mutations in the Protease Gene

Once the protease gene has been cloned and desirable sites for mutagenesis identified, the mutations can be introduced using synthetic oligonucleotides. These oligonucleotides contain nucleotide sequences flanking the desired mutation sites, mutant nucleotides are inserted during oligonucleotide synthesis. In a preferred method, a single stranded gap of DNA, bridging the protease gene, is created in a vector bearing the protease gene. Then the synthetic nucleotide, bearing the desired mutation, is annealed to a homologous portion of the single-stranded DNA. The remaining gap is then filled in by DNA polymerase I (Klenow fragment), and the construct is ligated using T4 ligase. A specific example of this method is described [Morinaga et al., Biotechnology, 1984 2 646–639]. According to Morinaga et al., a fragment within the gene is removed using restriction endonuclease. The vector/gene, now containing a gap, is then denatured and hybridized to a vector/ gene which, instead of containing a gap, has been cleaved with another restriction endonuclease at a site outside the area involved in the gap. A single-stranded region of the gene is then available for hybridization with mutated oligonucleotides, the remaining gap is filled in by the Klenow fragment of DNA polymerase I, the insertions are ligated with T4 DNA ligase, and, after one cycle of replication, a double-stranded plasmid bearing the desired mutation is produced. The Morinaga method obviates the additional manipulation of constructing new restriction sites, and, therefore, facilitates the generation of mutations at multiple sites. U.S. Pat. No. 4,760,025 discloses the introduction of oligonucleotides bearing multiple mutations by performing minor alterations of the cassette. However, an even greater variety of mutations can be introduced at any one time by the Morinaga method, because a multitude of oligonucleotides, of various lengths, can be introduced.

Expression of Protease Variants

According to the invention, a mutated protease gene produced by methods described above, or any alternative methods known in the art, can be expressed, in enzyme form, using an expression vector. An expression vector generally falls under the definition of a cloning vector, since an expression vector usually includes the components of a typical cloning vector, namely an element that permits autonomous replication of the vector in a microorganism independent of the genome of the microorganism, and one or more phenotypic markers for selection purposes. An expression vector includes control sequences encoding a promoter, operator, ribosome binding site, translation initiation signal, and, optionally, a repressor gene or various activator genes.

To permit the secretion of the expressed protein, nucleotides encoding a "signal sequence" may be inserted prior to the coding sequence of the gene. For expression under the direction of control sequences, a target gene to be treated according to the invention is operably linked to the control sequences in the proper reading frame. Promoter sequences that can be incorporated into plasmid vectors, and which can support the transcription of the mutant protease gene, include but are not limited to the prokaryotic β-lactamase promoter [Villa-Kamaroff, et al., Proc. Natl. Acad. Sci. U.S.A., 1978 75 3727–3731] and the tac promoter [DeBoer, et al., Proc. Natl. Acad. Sci. U.S.A., 1983 80 21–25]. Further references can also be found in "Useful proteins from recombinant bacteria" in Scientific American, 1980 242 74–94.

According to one embodiment, *B. subtilis* is transformed by an expression vector carrying the mutated DNA. If expression is to take place in a secreting microorganism such as *B. subtilis*, a-signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when it is present.

The microorganisms able to produce a stabilized enzyme of this invention can be cultivated by conventional fermentation methods in a nutrient medium containing assimilable carbon and nitrogen together with other essential nutrients, the medium being composed in accordance with the principles of the known art.

The protease variant protein secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

Nucleotide Sequences, Expression Vectors and Microorganisms

This invention also relates to DNA nucleotide sequences encoding a stabilized protease variant of the invention. The stabilized enzyme variant may be expressed and produced when DNA nucleotide sequence encoding this enzyme is inserted into a suitable vector in a suitable host organism. The host organism is not necessarily identical to the organism from which the parent gene originated.

The invention also relates to expression vectors and host organisms containing a DNA nucleotide encoding a stabilized protease variant of this invention.

Detergent Compositions

According to the invention, the protease variant may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% of water and 0–30% of organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylase, cellulase, cutinase, lipase, peroxidase, or oxidase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxy acids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

| 1) A detergent composition formulated as a granulate having a bulk density of at least 600 g/l comprising | |
|---|---|
| linear alkylbenzenesulfonate (calculated as acid) | 7–12% |
| alcohol ethoxysulfate (e.g., $C_{12-18}$ alcohol, 1–2 EO) or alkyl sulfate (e.g., $C_{16-18}$) | 1–4% |
| alcohol ethoxylate (e.g., $C_{14-15}$ alcohol, 7 EO) | 5–9% |
| sodium carbonate (as $Na_2CO_3$) | 14–20% |
| soluble silicate (as $Na_2O$, $2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g., maleic/acrylic acid copolymer; PVP, PEG) | 0–3% |
| enzymes | 0–5% |
| minor ingredients (e.g., suds supressors, perfume, optical brightener, photobleach) | 0–5% |
| 2) A detergent composition formulated as a granulate having a bulk density of at least 600 g/l comprising | |
| linear alkylbenzenesulfonate (calculated as acid) | 6–11% |
| alcohol ethoxysulfate (e.g., $C_{12-18}$ alcohol, 1–2 EO) or alkyl sulfate (e.g., $C_{16-18}$) | 1–3% |
| alcohol ethoxylate (e.g., $C_{14-15}$ alcohol, 7 EO) | 5–9% |
| sodium carbonate (as $Na_2CO_3$) | 15–21% |
| soluble silicate (as $Na_2O$, $2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g., maleic/acrylic acid copolymer, PVP, PEG) | 1–6% |
| enzymes | 0–5% |
| minor ingredients (e.g., suds supressors, perfume) | 0–5% |
| 3) A detergent composition formulated as a granulate having a bulk density of at least 600 g/l comprising | |
| linear alkylbenzenesulfonate (calculated as acid) | 5–9% |
| alcohol ethoxylate (e.g., $C_{12-15}$ alcohol, 7 EO) | 7–14% |
| soap as fatty acid (e.g., $C_{16-22}$) | 1–3% |
| sodium carbonate (as $Na_2CO_3$) | 10–17% |
| soluble silicate (as $Na_2O$, $2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g., EDTMPA) | 0–1% |
| carboxymethylcellulose | 0–2% |
| polymers (e.g., maleic/acrylic acid copolymer, PVP, PEG) | 1–3% |
| enzymes | 0–5% |
| minor ingredients (e.g., suds supressors, perfume, optical brightener) | 0–5% |
| 4) A detergent composition formulated as a granulate having a bulk density of at least 600 g/l comprising | |
| linear alkylbenzenesulfonate (calculated as acid) | 8–12% |
| alcohol ethoxylate (e.g., $C_{12-15}$ alcohol, 7 EO) | 10–25% |
| sodium carbonate (as $Na_2CO_3$) | 14–22% |
| soluble silicate (as $Na_2O$, $2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g., maleic/acrylic copolymer, PVP, PEG) | 1–3% |
| enzymes | 0–5% |
| minor ingredients (e.g., suds suppressors, perfume) | 0–5% |
| 5) An aqueous liquid detergent composition comprising | |
| linear alkylbenzenesulfonate (calculated as acid) | 15–21% |
| alcohol ethoxylate (e.g., $C_{12-15}$ alcohol, 7 EO or $C_{12-15}$ alcohol, 5 EO) | 12–18% |
| soap as fatty acid (e.g., oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g., PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g., dispersants, suds suppressors, perfume, optical brightener) | 0–5% |
| 6) An aqueous structured liquid detergent composition comprising | |
| linear alkylbenzenesulfonate (calculated as acid) | 15–21% |
| alcohol ethoxylate (e.g., $C_{12-15}$ alcohol, 7 EO or $C_{12-15}$ alcohol, 5 EO) | 3–9% |
| soap as fatty acid (e.g., oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g., PEG, PVP) | 0–3% |
| anchoring polymers as e.g., lauryl methacrylate/acrylic acid copolymer; | 0–3% |

-continued

| | |
|---|---|
| molar ratio 25:1; MW 3800 | |
| glycerol | 0–5% |
| enzymes | 0–5% |
| minor ingredients | 0–5% |
| (e.g., dispersants, suds supressors, perfume, optical brighteners) | |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as $Na_2CO_3$) | 5–10% |
| soluble silicate (as $Na_2O, 2SiO_2$) | 1–4% |
| zeolite (as $NaAlSiO_4$) | 20–40% |
| sodium sulfate (as $Na_2SO_4$) | 2–8% |
| sodium perborate (as $NaBO_3.H_2O$) | 12–18% |
| TAED | 2–7% |
| polymers (e.g., maleic/acrylic acid copolymer, PEG) | 1–5% |
| enzymes | 0–5% |
| minor ingredients (e.g., optical brightener, suds supressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as $Na_2CO_3$) | 4–10% |
| soluble silicate (as $Na_2O, 2SiO_2$) | 1–4% |
| zeolite (as $NaAlSiO_4$) | 30–50% |
| sodium sulfate (as $Na_2SO_4$) | 3–11% |
| sodium citrate (as $C_6H_5Na_3O_7$) | 5–12% |
| polymers (e.g., PVP, maleic/acrylic acid copolymer, PEG) | 1–5% |
| enzymes | 0–5% |
| minor ingredients (e.g., suds supressors, perfume) | 0–5% |

9) A detergent composition formulated as a granulate comprising

| | |
|---|---|
| linear alkylbenzenesulfonate (calculated as acid) | 6–12% |
| nonionic surfactant, | 1–4% |
| soap as fatty acid | 2–6% |
| sodium carbonate (as $Na_2CO_3$) | 14–22% |
| zeolite (as $NaAlSiO_4$) | 18–32% |
| sodium sulfate (as $Na_2SO_4$) | 5–20% |
| sodium citrate (as $C_6H_5Na_3O_7$) | 3–8% |
| sodium perborate (as $NaBO_3.H_2O$) | 4–9% |
| bleach activator (e.g., NOBS or TAED) | 1–5% |
| carboxymethylcellulose | 0–2% |
| polymers (e.g., polycarboxylate or PEG) | 1–5% |
| enzymes | 0–5% |
| minor ingredients (e.g., optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g., $C_{12-15}$ alcohol, 2–3 EO) | 8–15% |
| alcohol ethoxylate (e.g., $C_{12-15}$ alcohol, 7 EO or $C_{12-15}$ alcohol, 5 EO) | 3–9% |
| soap as fatty acid (e.g., lauric acid) | 0–3% |
| aminoethanol | 1–5% |
| sodium citrate | 5–10% |
| hydrotrope (e.g., sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g., polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g., $C_{12-15}$ alcohol, 7 EO or $C_{12-15}$ alcohol, 5 EO) | 6–12% |
| aminoethanol | 2–6% |
| citric acid | 8–14% |
| borate (as $B_4O_7$) | 1–3% |
| polymer (e.g., maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g., hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha–olefinsulfonate, alpha-sulfo fatty acid methyl esters, alkanesulfonates, soap) | 25–40% |
| nonionic surfactant (e.g., alcohol ethoxylate) | 1–10% |
| sodium carbonate (as $Na_2CO_3$) | 8–25% |
| soluble silicates (as $Na_2O, 2SiO_2$) | 5–15% |
| sodium sulfate (as $Na_2SO_4$) | 0–5% |
| zeolite (as $NaAlSiO_4$) | 15–28% |
| sodium perborate (as $NaBO_3.4H_2O$) | 0–20% |
| bleach activator (TAED or NOBS) | 0–5% |
| enzymes | 0–5% |
| minor ingredients (e.g., perfume, optical brighteners) | 0–3% |

13) Detergent formulations as described in 1)–12) where the content of linear alkylbenzenesulfonate—or a part of it—is substituted by alkyl sulfate ($C_{12}$–$C_{18}$).

14) Detergent formulations as described in 1)–13) which contain a stabilized or encapsulated peracid either as an additional component or as a substitute for already specified bleach systems.

15) Detergent compositions as described in 3), 7), 9) and 12) where the content of perborate is substituted with percarbonate.

16) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

The protease variant of the invention may be incorporated in concentrations conventionally employed in detergents. It is at present contemplated that, in the detergent composition of the invention, the protease variant may be added in an amount corresponding to 0.001–100 mg of protease variant per liter of wash liquor.

The following examples further illustrate the present invention, and they are not intended to be in any way limiting to the scope of the invention as claimed.

EXAMPLE 1

The Peroxidase System

A peroxidase (POD) system used for Dye Transfer Inhibition (DTI), comprising a *Coprinus cinereus* peroxidase (CiP, obtained according to EP Patent Application 179,486), hydrogen peroxide ($H_2O_2$), and p-hydroxybenzenesulfonate (pHBS) as peroxidase enhancing agent, was simulated in a sodium phosphate buffer:

[pHBS]: 50 μM, [$H_2O_2$]: 200 μM, [CiP]: 2 PODU/ml, 20 mM sodium phosphate, pH 8.5.

The activity of Subtilisin 309 (Savinase®, supplied by Novo Nordisk A/S Denmark) was investigated after incubation with the peroxidase system for 20 min. at 35° C.

The residual activity of Subtilisin 309 was measured using the substrate N-succinyl-Ala-Ala-Pro-Phe-p-nitroanilide, as described above. The stability of the protease was evaluated analytically using concentrations of 40' nM and 400 nM, respectively.

For both concentrations the residual activity of Subtilisin 309 was measured to 15% relative to untreated Subtilisin 309. The Subtilisin thus clearly becomes inactivated in the presence of the POD system.

EXAMPLE 2

Subtilisin 309 was incubated with the POD system in the presence of [$^{14}$C]-pHBS as described in Example 1. After POD treatment Subtilisin 309 was purified and subjected to further investigation by amino acid analysis and gelfiltration chromatography under denaturing conditions.

Purification of POD Treated Subtilisin 309

Two liters of sodium phosphate buffer containing the POD system and Subtilisin 309 in a concentration of 400 nM were incubated for 20 min. at 35° C. After inactivation the solution was concentrated to 3 ml in Amicon cells using YM10 membranes (Amicon). Further purification was performed on a gelfiltration column; Superdex 75 (16/60) eluted with 0.1 M ammonium acetate. The largest part of the POD treated Subtilisin 309 eluted with a molecular weight slightly higher than untreated Subtilisin 309. The POD treated Subtilisin 309 was concentrated and washed with 10 volumes of Milli Q water in an Amicon cell.

Amino Acid Analysis

Amino acid analysis was carried out in the Applied Biosystems 420A amino acid analysis system according to the manufacturers instructions.

The results from the amino acid analysis are presented in Table 1 below. As can be seen from the Table, the only detectable amino acid that is affected significantly by POD inactivation is tyrosine (Tyr).

POD inactivation of Subtilisin 309 in the presence of [$^{14}$C]-pHBS results in radioactive labelling of the enzyme. The covalent nature of this modification has been shown through gelfiltration under denaturing conditions in 2 M urea.

TABLE 1

Amino acid analysis of Subtilisin 309 and POD inactivated Subtilisin 309.

|     | POD inactivated Subtilisin 309 | Subtilisin 309 | Subtilisin 309 (theoretical) |
|-----|---|---|---|
| Asx | 31 | 31 | 27 |
| Glx | 17 | 18 | 15 |
| Ser | 34 | 30 | 34 |
| Gly | 35 | 36 | 35 |
| His | 8 | 7 | 7 |
| Arg | 10 | 10 | 8 |
| Thr | 17 | 16 | 17 |
| Ala | 41 | 39 | 40 |
| Pro | 14 | 14 | 13 |
| Tyr | 3 | 8 | 7 |
| Val | 23 | 23 | 25 |
| Met[a] | 2 | 1 | 3 |
| Cys | 0 | 0 | 0 |
| Ile | 8 | 8 | 9 |
| Leu | 20 | 19 | 19 |
| Phe | 2 | 2 | 2 |
| Lys | 6 | 6 | 5 |
| Trp[b] | ND[c] | ND[c] | 3 |

[a]Methionine cannot be quantitatively determined following acid hydrolysis
[b]Tryptophan is completely destroyed during acid hydrolysis
[c](ND, not determined).

EXAMPLE 3

The stabilization of Subtilisin 309 towards the peroxidase system has been investigated using several variants in which one or more tyrosines were substituted by other amino acid residues.

The peroxidase system was simulated in a Britton-Robinson buffer using 7-hydroxycoumarin (7HCm) as peroxidase enhancing agent:

[7HCm]: 10 µM, [H$_2$O$_2$]: 200 µM, [CiP]: 2 PODU/ml, 20 mM Britton-Robinson buffer (20 mM sodium acetate, 20 mM sodium borate and 20 mM sodium phosphate), pH 8.5.

The different variants were incubated with the peroxidase system in concentrations varying from 80 to 120 nM. After incubation for 10 min. at 35° C. the residual activity of the variants was analyzed using the substrate N-succinyl-Ala-Ala-Pro-Phe-p-nitroanilide, as described above. The residual activities were measured relative to untreated variants.

The results are presented in Table 2 below. As can be seen from the Table, the two variants containing substitutions in positions 167, 171, and 192 are significantly stabilized towards the peroxidase system using 7HCm as enhancer.

TABLE 2

Residual activity of Subtilisin 309 variants after incubation with the POD system for 10 min.

| Variants | Residual activity (%) |
|---|---|
| Sub. 309 | 21[a] ± 3 |
| Sub. 309/Y167F + Y171V + Y192F | 46 ± 5 |
| Sub. 309/K235R + K237R + Y263F | 31 ± 4 |
| Sub. 309/Y209F + Y214F | 25 ± 3 |
| Sub. 309/Y167F + Y171V + Y192F + Y209Q + Y214Q | 41 ± 6 |

[a]mean ± SD, n = 6

EXAMPLE 4

Several of the Subtilisins mentioned above contain a tyrosine residue in position.104. The importance of a tyrosine in this position was investigated using the Subtilisin 309 variant V104Y.

The peroxidase system was simulated in a Britton-Robinson buffer using 7-hydroxycoumarin (7HCm) as peroxidase enhancing agent:

[7HCm]: 5 µM, [H$_2$O$_2$]: 200 µM, [CiP]: 2 PODU/ml, 20 mM Britton-Robinson buffer (20 mM sodium acetate, 20 mM sodium borate and 20 mM sodium phosphate), pH 8.5.

The proteases were incubated with the peroxidase system in a concentration of 80 nM. After incubation for 1, 5, and 10 min. at 35° C., the residual activities of the proteases were analyzed using the N-succinyl-Ala-Ala-Pro-Phe-p-nitroanilide substrate, as described above. The residual activities were measured relative to untreated variants.

The results are presented in FIG. 1. After the introduction of an additional tyrosine in position 104, the Subtilisin 309 variant became much more sensitive towards the POD system.

What is claimed is:

1. A protease variant comprising a Tyr residue at one of positions 91, 167, 171, 192, 209, 214, or 263 (BPN' numbering), wherein Tyr 91 is substituted with Leu, Ile, Val, Gln, Asn, Ser, Thr, Glu, or His; Tyr 167 is substituted with Leu, Ile, Gln, Asn, Ser, Thr, or His; Tyr 171 is substituted with Phe, Leu, Ile, Gln, Asn, Ser, or His; Tyr 192 is substituted with Leu, Ile, Gln, Asn, Ser, Thr, or His; Tyr 209 is substituted with Ile, Val, Gln, Asn, Ser, Thr, Glu, or His; Tyr 214 is substituted with Phe, Leu, Ile, Val, Gln, Asn, Glu, or His; or Tyr 263 is substituted at Leu, Ile, Val, Gln, Asn, Ser, Thr, Glu, or His.

2. The protease variant of claim 1 derived from *Bacillus lentus*.

3. The protease variant of claim 2 derived from one of Subtilisin 309 or Subtilisin 147.

4. The protease variant of claim 1 derived from *Bacillus amyloliquefaciens*.

5. The protease variant of claim 4 derived from Subtilisin BPN'.

6. The protease variant of claim 1 derived from *Bacillus licheniformis*.

7. The protease variant of claim 1 derived from Subtilisin Carlsberg.

8. A detergent composition comprising:
(a) a protease variant comprising a Tyr residue at one of positions 91, 167, 171, 192, 209, 214, or 263 (BPN' numbering), wherein Tyr 91 is substituted with Leu, Ile, Val, Gln, Asn, Ser, Thr, Glu, or His; Tyr 167 is substituted with Leu, Ile, Gln, Asn, Ser, Thr, or His; Tyr 171 is substituted with Phe, Leu, Ile, Gln, Asn, Ser, or His; Tyr 192 is substituted with Leu, Ile, Gln, Asn, Ser, Thr, or His; Tyr 209 is substituted with Ile, Val, Gln, Asn, Ser, Thr, Glu, or His; Tyr 214 is substituted with Phe, Leu, Ile, Val, Gln, Asn, Glu, or His; or Tyr 263 is substituted at Leu, Ile, Val, Gln, Asn, Ser, Thr, Glu, or His; and
(b) a surfactant.

* * * * *